United States Patent
Damavandi

(10) Patent No.: US 11,998,704 B2
(45) Date of Patent: Jun. 4, 2024

(54) ELECTRIC DIFFUSER APPARATII

(71) Applicant: DAJ GLOBAL PARTNERS LLC, Los Angeles, CA (US)

(72) Inventor: David Damavandi, Los Angeles, CA (US)

(73) Assignee: DAJ GLOBAL PARTNERS LLC, Los Angeles, CA (US)

( * ) Notice: Subject to any disclaimer, the term of this patent is extended or adjusted under 35 U.S.C. 154(b) by 869 days.

(21) Appl. No.: 16/952,022

(22) Filed: Nov. 18, 2020

(65) Prior Publication Data

US 2021/0353902 A1    Nov. 18, 2021

Related U.S. Application Data

(63) Continuation-in-part of application No. 29/735,080, filed on May 18, 2020, now Pat. No. Des. 977,082.

(51) Int. Cl.
*A61M 21/02* (2006.01)
*A61M 21/00* (2006.01)

(52) U.S. Cl.
CPC ..... *A61M 21/02* (2013.01); *A61M 2021/0016* (2013.01); *A61M 2205/36* (2013.01); *A61M 2205/8237* (2013.01); *A61M 2209/084* (2013.01)

(58) Field of Classification Search
CPC .......... A61M 21/02; A61M 2021/0016; A61M 2205/36; A61M 2205/8237; A61M 2209/084
USPC ......................................................... 239/34
See application file for complete search history.

(56) References Cited

U.S. PATENT DOCUMENTS

| | | | | |
|---|---|---|---|---|
| 4,603,030 A | * | 7/1986 | McCarthy | A61L 9/122 261/DIG. 65 |
| 4,629,604 A | * | 12/1986 | Spector | A01M 1/2077 360/79 |
| 4,952,024 A | * | 8/1990 | Gale | A63F 13/53 359/477 |
| 5,565,148 A | * | 10/1996 | Pendergrass, Jr. | A61L 9/125 261/DIG. 65 |
| 6,024,783 A | * | 2/2000 | Budman | H04N 7/08 261/DIG. 65 |
| 6,713,024 B1 | * | 3/2004 | Arnell | A61L 9/125 239/57 |

* cited by examiner

*Primary Examiner* — Chee-Chong Lee
(74) *Attorney, Agent, or Firm* — ORBIT IP, LLP

(57) ABSTRACT

Electric diffuser apparatus are provided herein. The diffuser apparatus includes a stand having a base, a container, a plate and a shaft extending along a longitudinal axis. The base having a first aperture extending through the base along the longitudinal axis, the container having a second aperture extending through the container along the longitudinal axis, and the plate having a third aperture extending through the plate along the longitudinal axis. The container is rotatably coupled to the base, and includes a plurality of compartments dimensioned for receiving a plurality of essential oil bottles. The shaft is hollow along the longitudinal axis with a first opening at a distal end and a second opening at a proximal end. The first aperture, the second aperture, the third aperture, the first opening and the second opening form a passage dimensioned to allow the power cord of the electric diffuser to pass therethrough.

16 Claims, 12 Drawing Sheets

ELECTRIC DIFFUSER APPARATII

CROSS REFERENCE TO RELATED APPLICATIONS

The present application is a continuation of and claims the benefit of priority to U.S. Design Patent Application No 29/735,080, filed May 18, 2020, which is hereby incorporated by reference in its entirety and is considered a part of this specification.

FIELD OF THE INVENTION

This patent document relates generally to electric diffuser apparatus. More particularly, the subject matter of this patent document relates to electric diffusers and stands for electric diffusers.

BACKGROUND

Electric diffusers are commonly used for aromatherapy, releasing fragrant essential oils in the air that provide a calmer and more pleasant experience. Although aromatherapy enhances psychological and physical well-being through smell, a person's well-being can also be affected by the other four senses: sight, hearing, taste and touch.

Diffusers that can affect at least two of the five senses are generally expensive. Moreover, the inclusion of one sense in a diffuser design can adversely reduce the effectiveness of another. For example, inclusion of speakers can reduce the aesthetic quality of the visual component. Thus, with an increased interest in enhanced aromatherapy experience, the need for improvements to affect at least two of the five senses still remains.

The present disclosure provides an improved electric diffuser apparatus with diffuser stands that, in addition to providing psychological and physical well-being through smell, enhances the aesthetic quality of the visual component by (a) masking the power cord of the electric diffuser to allow for the selection of an essential oil without the power cord getting in the way, and (b) visually displaying an array of essential oils for the user to enjoy and select from, which further enhances the quality of the touch component.

SUMMARY

Electric diffuser apparatus are provided herein. In one embodiment, the electric diffuser apparatus includes an electric diffuser and a diffuser stand. The electric diffuser has a power cord. The diffuser stand is adapted to mask the power cord while conveniently displaying an array of essential oil bottles for a user to select from.

In one embodiment, the diffuser stand may include a base, a container, a plate and a shaft. The base may include a first aperture extending through the base along a longitudinal axis of the diffuser stand. The container may be rotatably coupled to the base and having a plurality of compartments that may be arranged generally equidistant to a peripheral surface of the container. The plurality of compartments may be dimensioned for receiving a plurality of essential oil bottles. The container may also include a second aperture extending through the container along the longitudinal axis, while the plate may include a third aperture extending through the plate along the longitudinal axis. Further, the shaft may be hollow along the longitudinal axis and has a first opening at a distal end and a second opening at a proximal end. The shaft may be coupled to the base at the distal end with the first opening of the shaft aligned with the first aperture of the base along the longitudinal axis. Additionally, the shaft may also be coupled to the plate at the proximal end with the second opening of the shaft aligned with the third aperture of the plate along the longitudinal axis.

As can be appreciated, the electric diffuser may be positioned on the plate, and the power cord passes through the third aperture of the plate. The plate may include a peripheral portion, such as a rim, for receiving and/or securing the electric diffuser. In an embodiment, the shaft is configured and dimensioned to fit snugly within the third aperture of the plate and within the first aperture of the base. Further, the second aperture of the container may be dimensioned for receiving the shaft therethrough.

As can be appreciated, the first aperture, second aperture, third aperture, the first opening and the second opening form a passage dimensioned to allow the power cord to pass therethrough. In another embodiment, first aperture, second aperture, third aperture, the first opening and the second opening are concentric along the longitudinal axis of the diffuser stand.

Each of the foregoing various aspects, together with those set forth in the claims and described in connection with the embodiments summarized above and disclosed herein may be combined to form claims for an apparatus, system, methods of manufacture and/or use in any way disclosed herein without limitation.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

DETAILED DESCRIPTION

Figure 1:
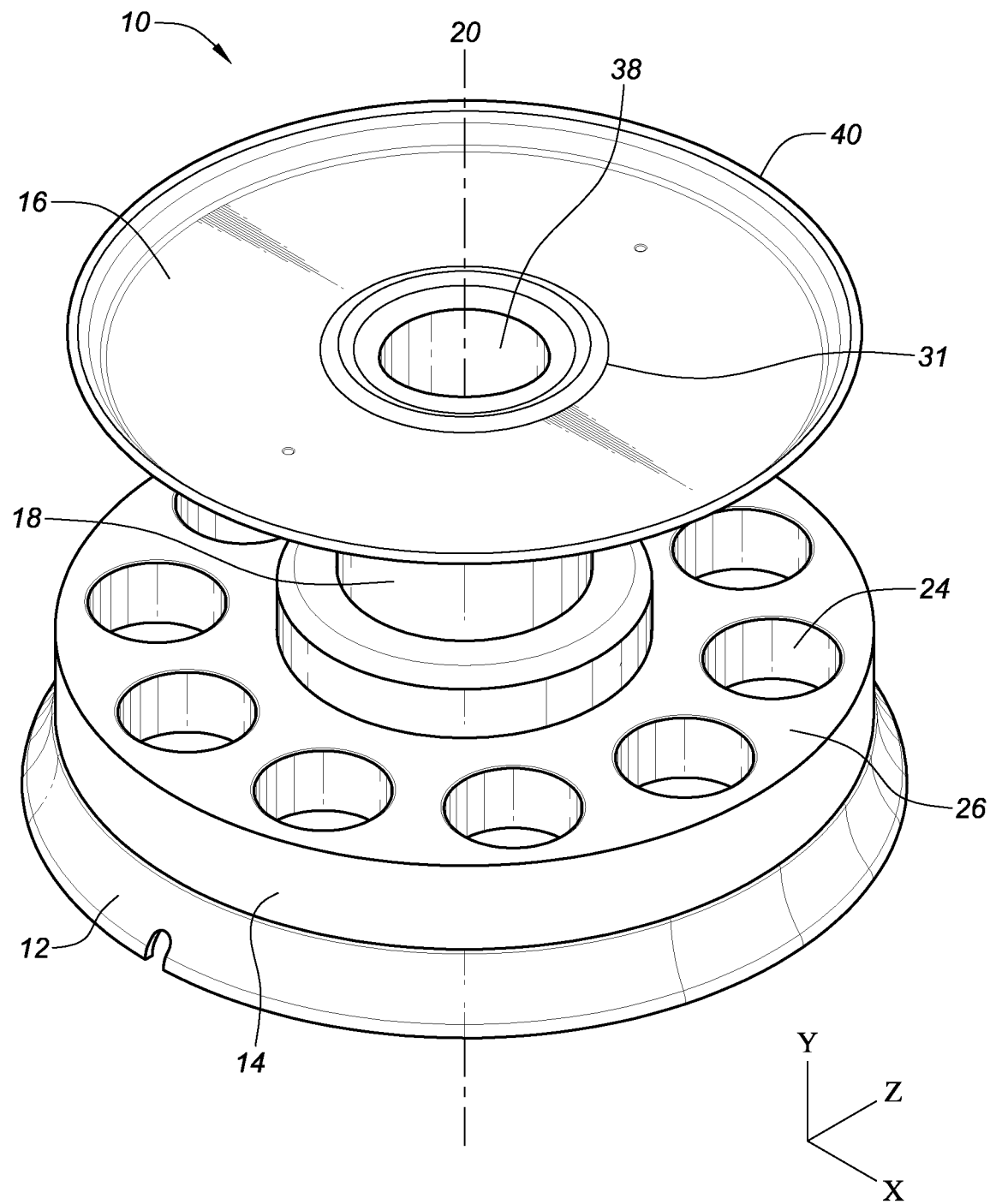
FIG. 1 is a first exemplary isometric view of a diffuser stand, according to an embodiment.
Figure 2:
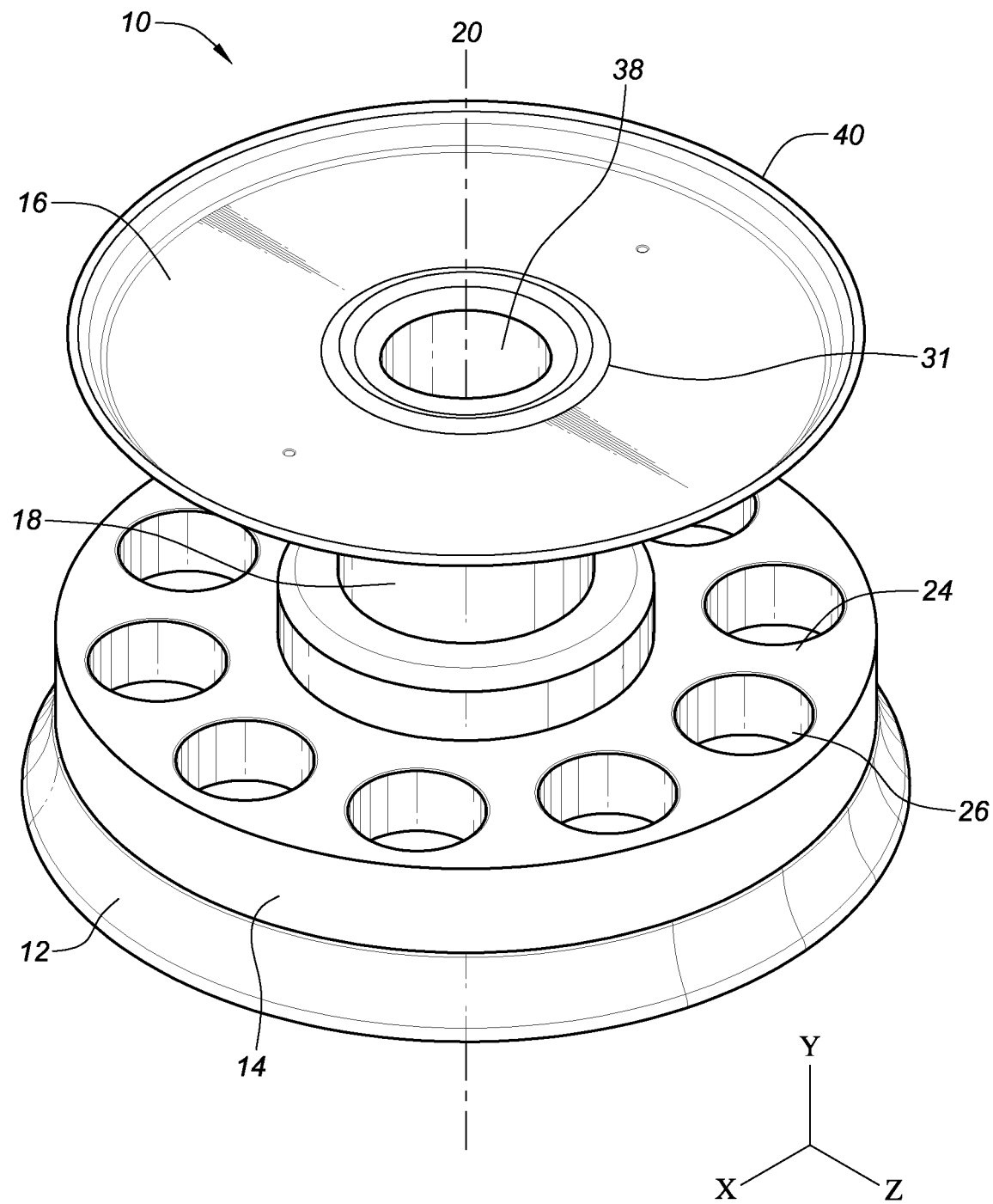
FIG. 2 is a second exemplary isometric view of the diffuser stand of FIG. 1, according to an embodiment.
Figure 3:
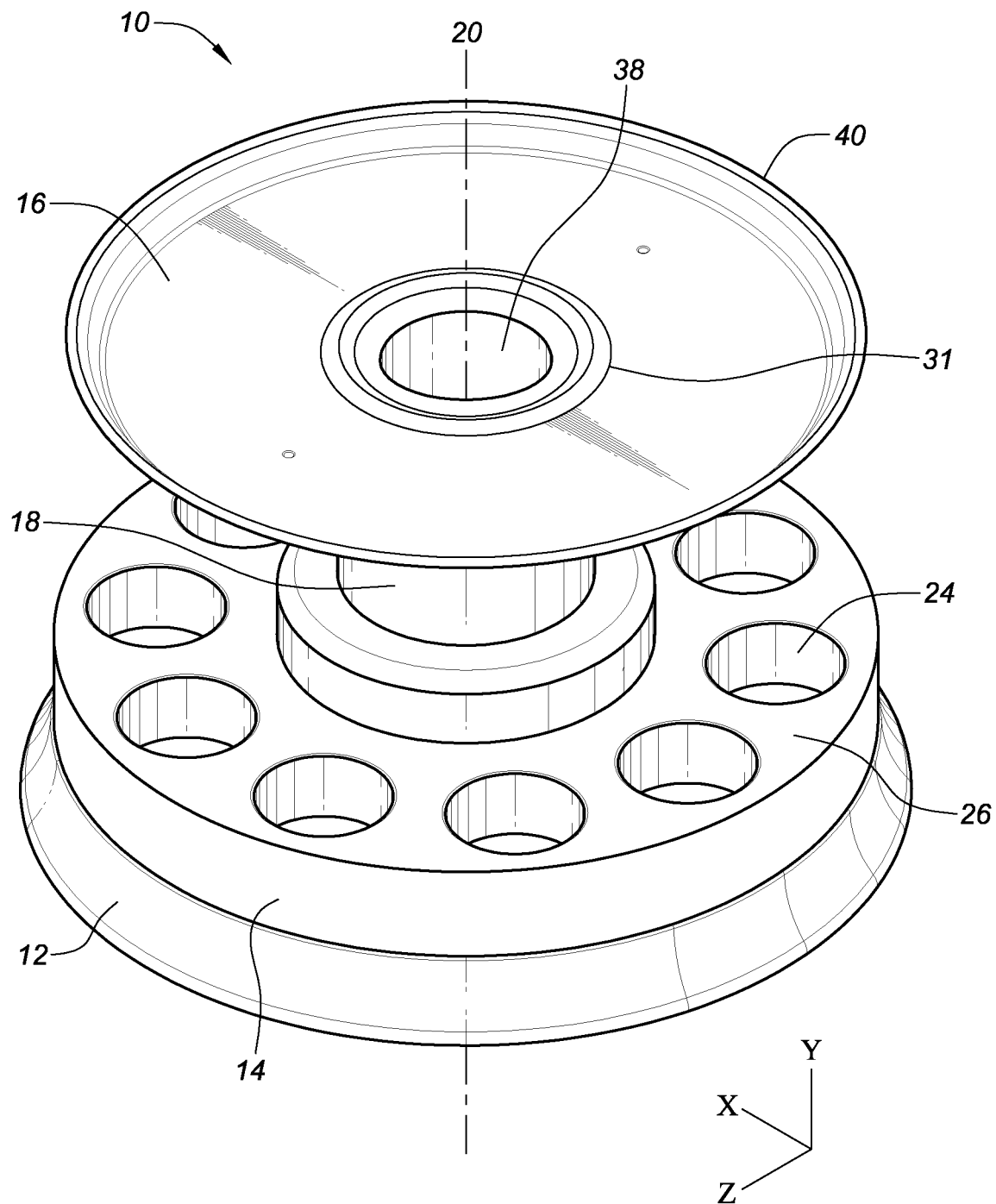
FIG. 3 is a third exemplary isometric view of the diffuser stand of FIG. 1, according to an embodiment.
Figure 4:
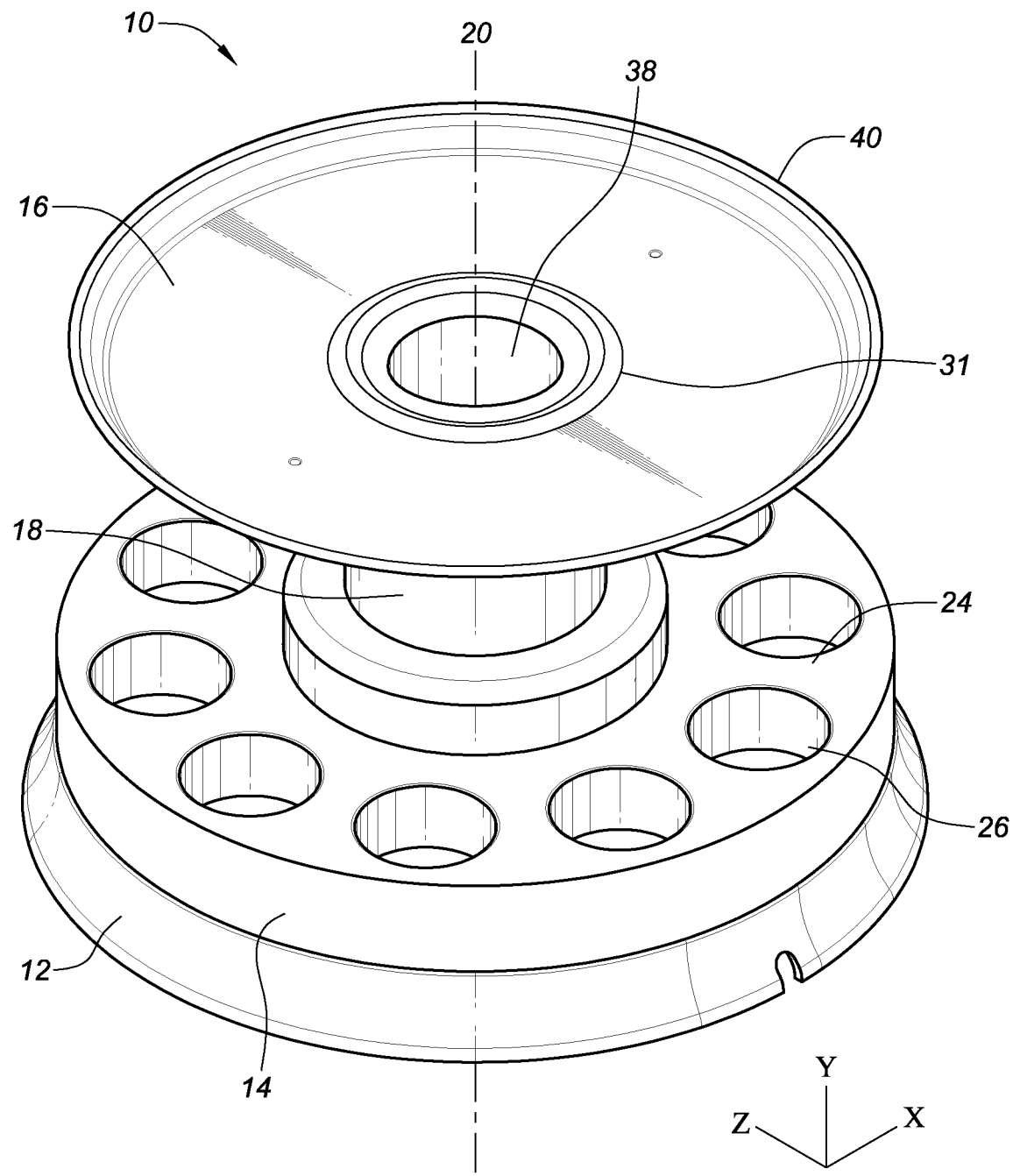
FIG. 4 is a fourth exemplary isometric view of the diffuser stand of FIG. 1, according to an embodiment.

Unique and inventive electric diffuser apparatus are disclosed herein. In one embodiment, an electric diffuser apparatus may include a diffuser stand for an electric diffuser. Although diffuser stand embodiments are disclosed herein, it is to be expressly understood that the present invention is not restricted solely to such embodiments. Rather, the present disclosure is directed to each of the inventive features described below, both individually as well as collectively, in various embodiments. Further, as will become apparent to those skilled in the art, one or more aspects of the present disclosure may be incorporated in other electronic devices.

FIGS. 1-12 disclose a diffuser stand 10 for an electric diffuser (not shown) with a power cord (not shown), according to an embodiment. The diffuser stand 10 may include a base 12, a container 14, a plate 16 and a shaft 18 extending along a longitudinal axis 20.

Figure 12:
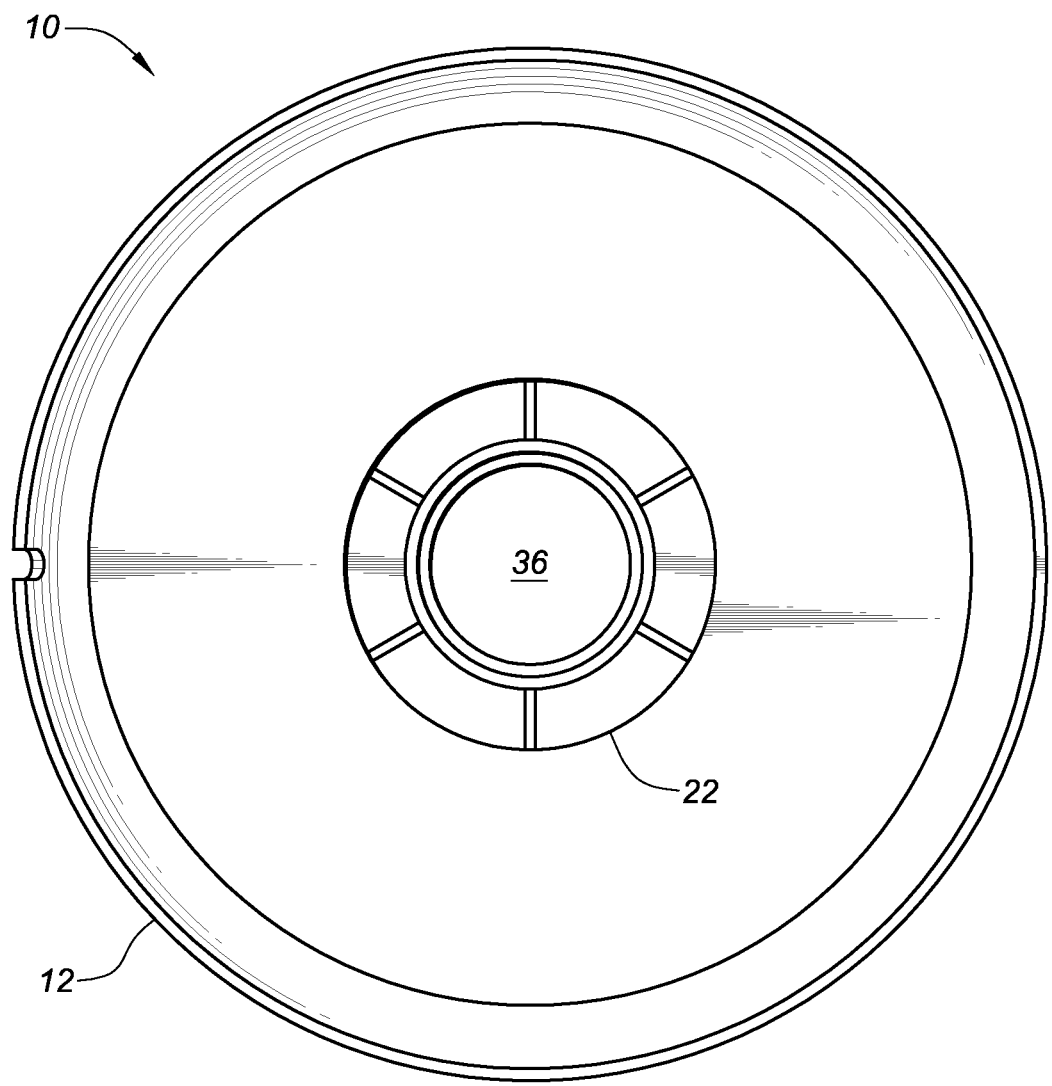
FIG. 12 is a bottom plan view of the diffuser stand of FIG. 1, according to an embodiment.

The base 12 may have a first aperture 22 (shown in FIG. 12) extending through the base 12 along the longitudinal axis 20 of the diffuser stand 10. As can be appreciated, the base 12 may be of any shape or configuration. In one embodiment, as shown in FIG. 12, the base 12 may have a circular cross-section.

Figure 5:
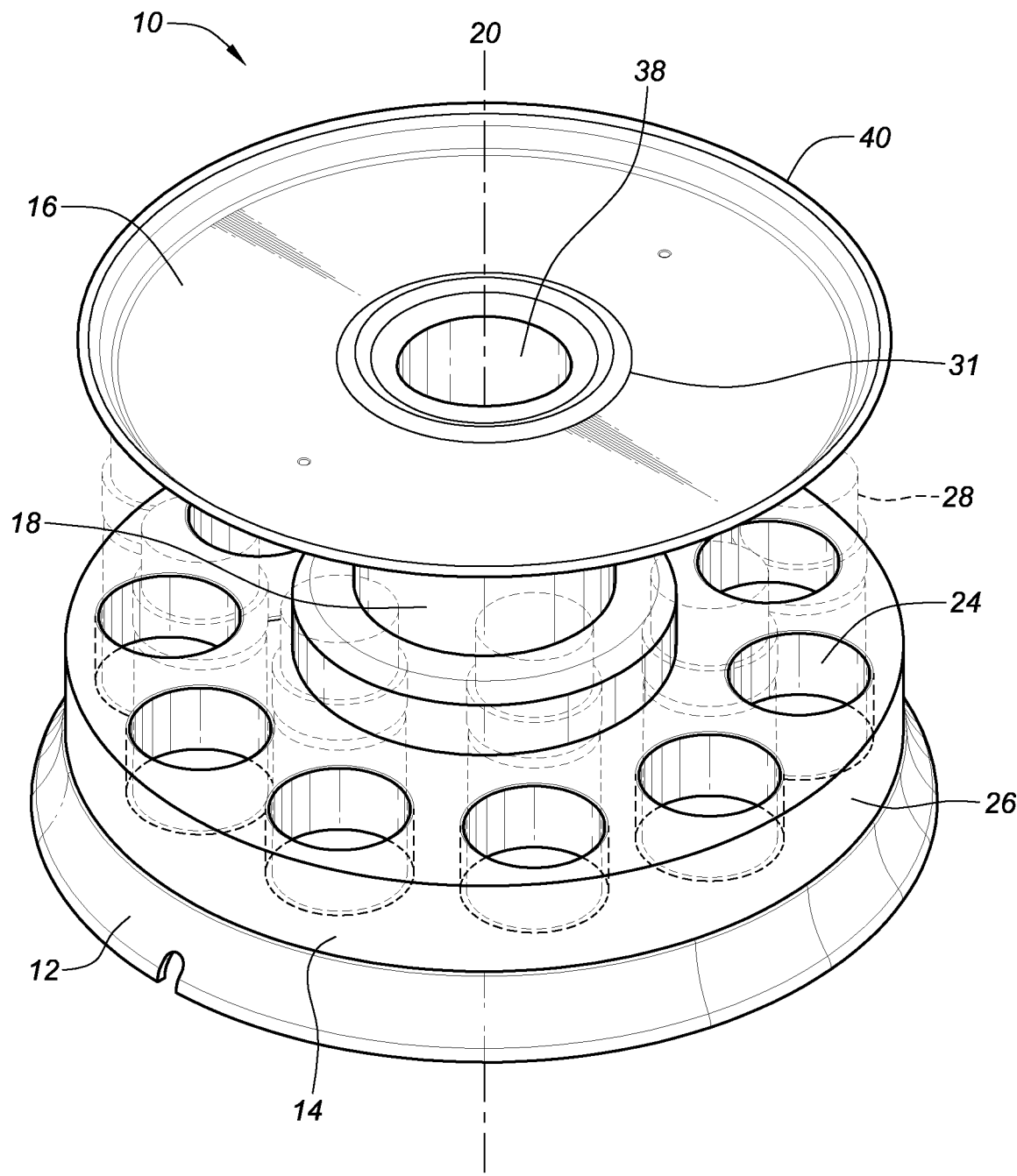
FIG. 5 is a fifth exemplary isometric view of the diffuser stand of FIG. 1, according to an embodiment.
Figure 6:
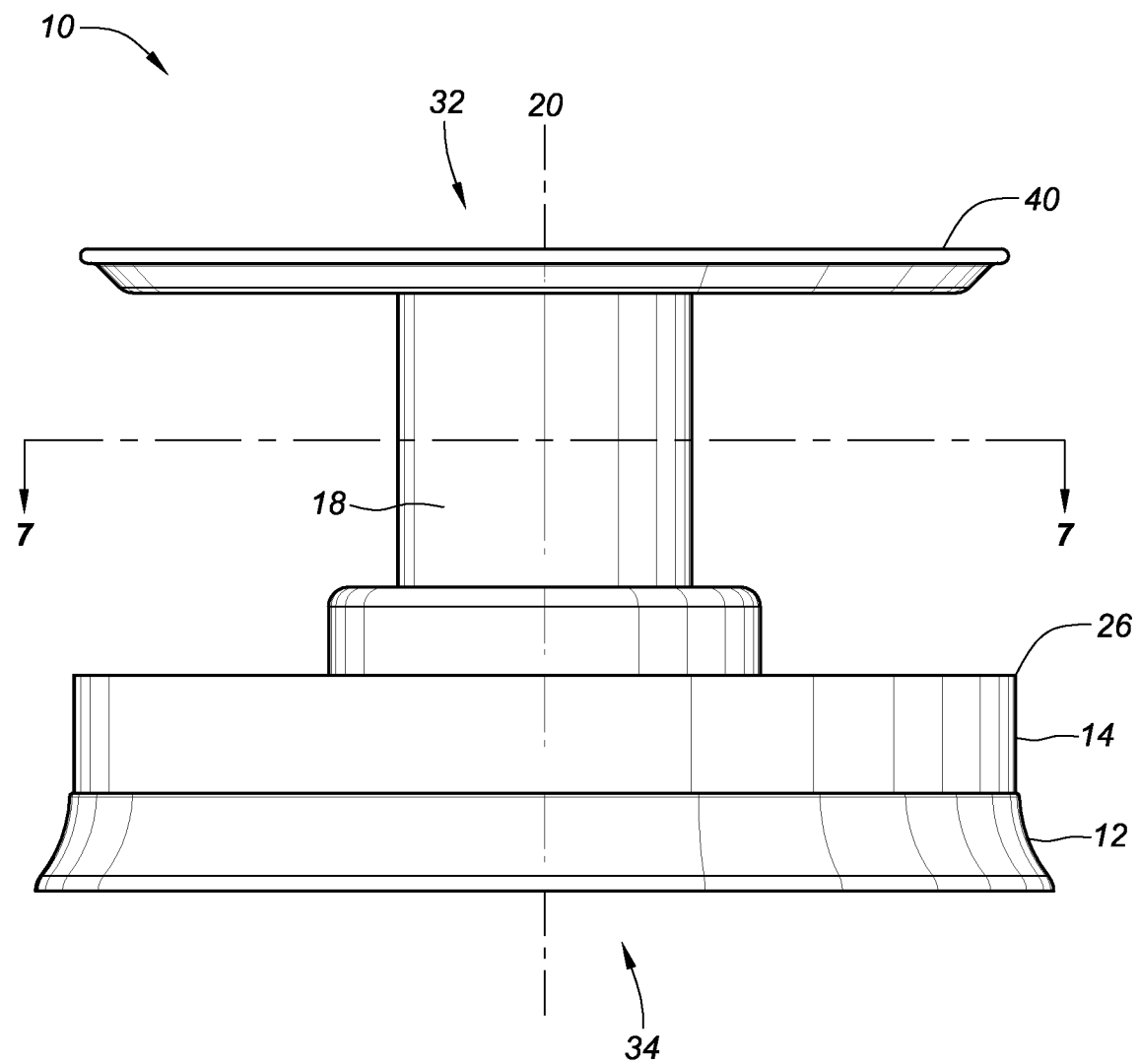
FIG. 6 is a left-side elevation view of the diffuser stand of FIG. 1, according to an embodiment.
Figure 7:
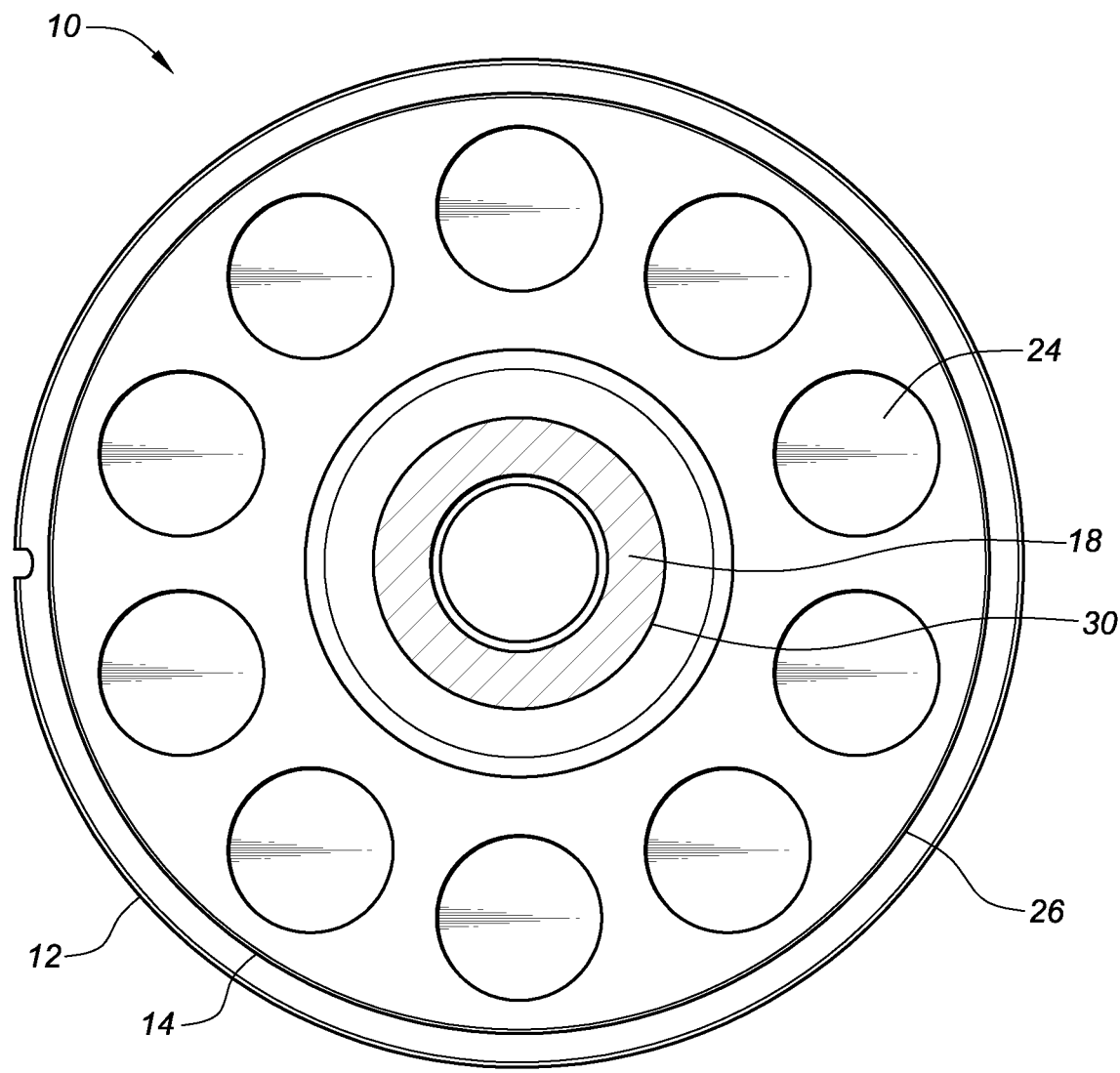
FIG. 7 is a cross-sectional view of the section 7-7 shown in FIG. 6, according to an embodiment.
Figure 8:
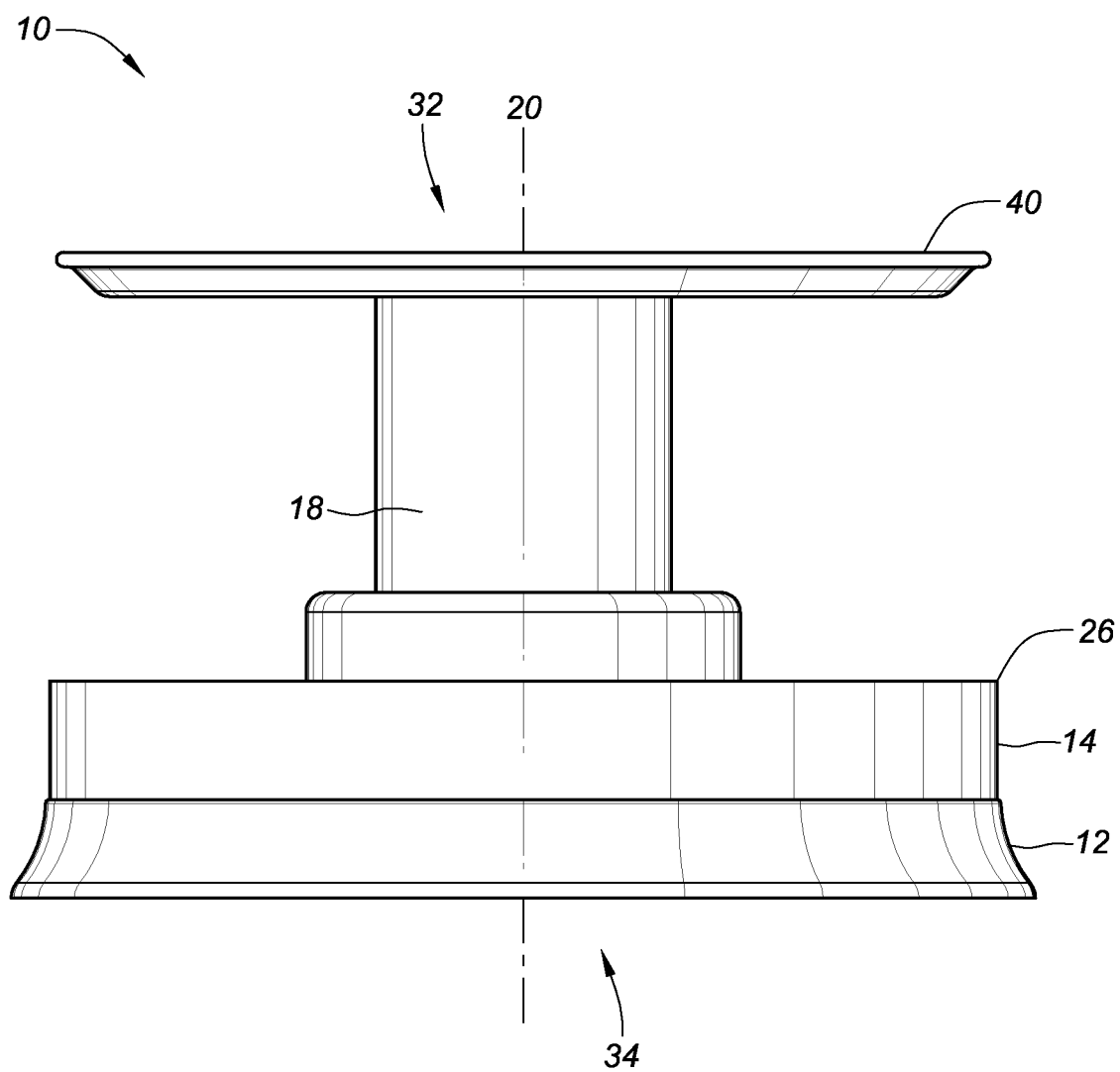
FIG. 8 is a right-side elevation view of the diffuser stand of FIG. 1, according to an embodiment.
Figure 9:
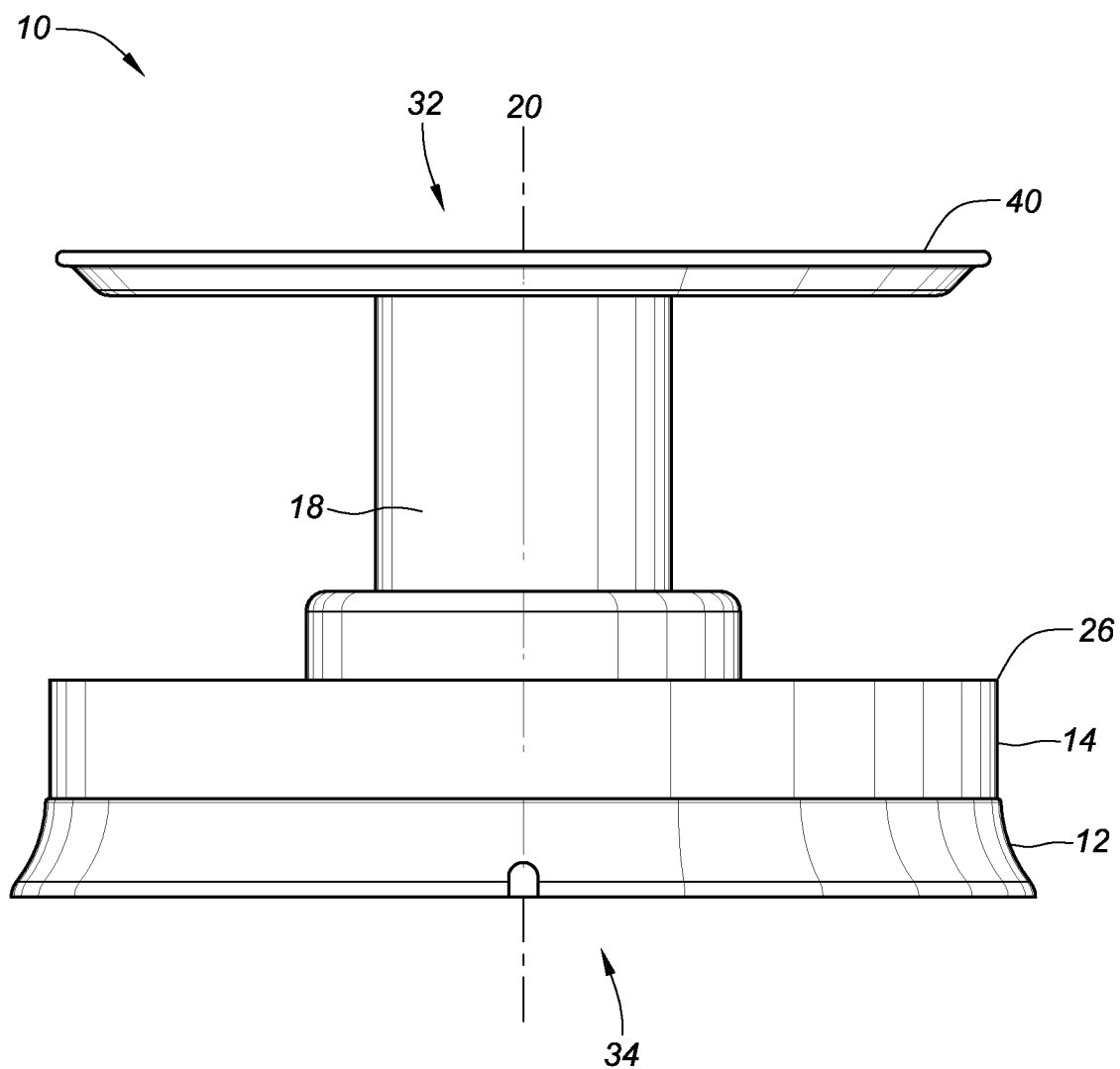
FIG. 9 is a front elevation view of the diffuser stand of FIG. 1, according to an embodiment.

Similarly, the container 12 may be of any shape or configuration. As shown in FIG. 1, the container 12 may be cylindrical with a plurality of compartments 24 that may be arranged generally equidistant to a peripheral cylindrical surface 26. In a preferred embodiment, the compartments 24 are arranged in a circle around the base that is concentric with the outside of the base. The plurality of compartments 24 may be so dimensioned for receiving a plurality of essential oil bottles 28, as shown in FIG. 5. In one embodiment, the compartments 24 may have a circular cross-section for receiving cylindrical essential oil bottles 28. As can be appreciated, such configuration provides a convenient display of an array of essential oils for the user to enjoy and select therefrom. The container 12 may also include a second aperture 30 (shown in FIG. 7) extending through the container 12 along the longitudinal axis 20. In one embodiment, the container 12 may be rotatably coupled to the base 12.

Figure 11:
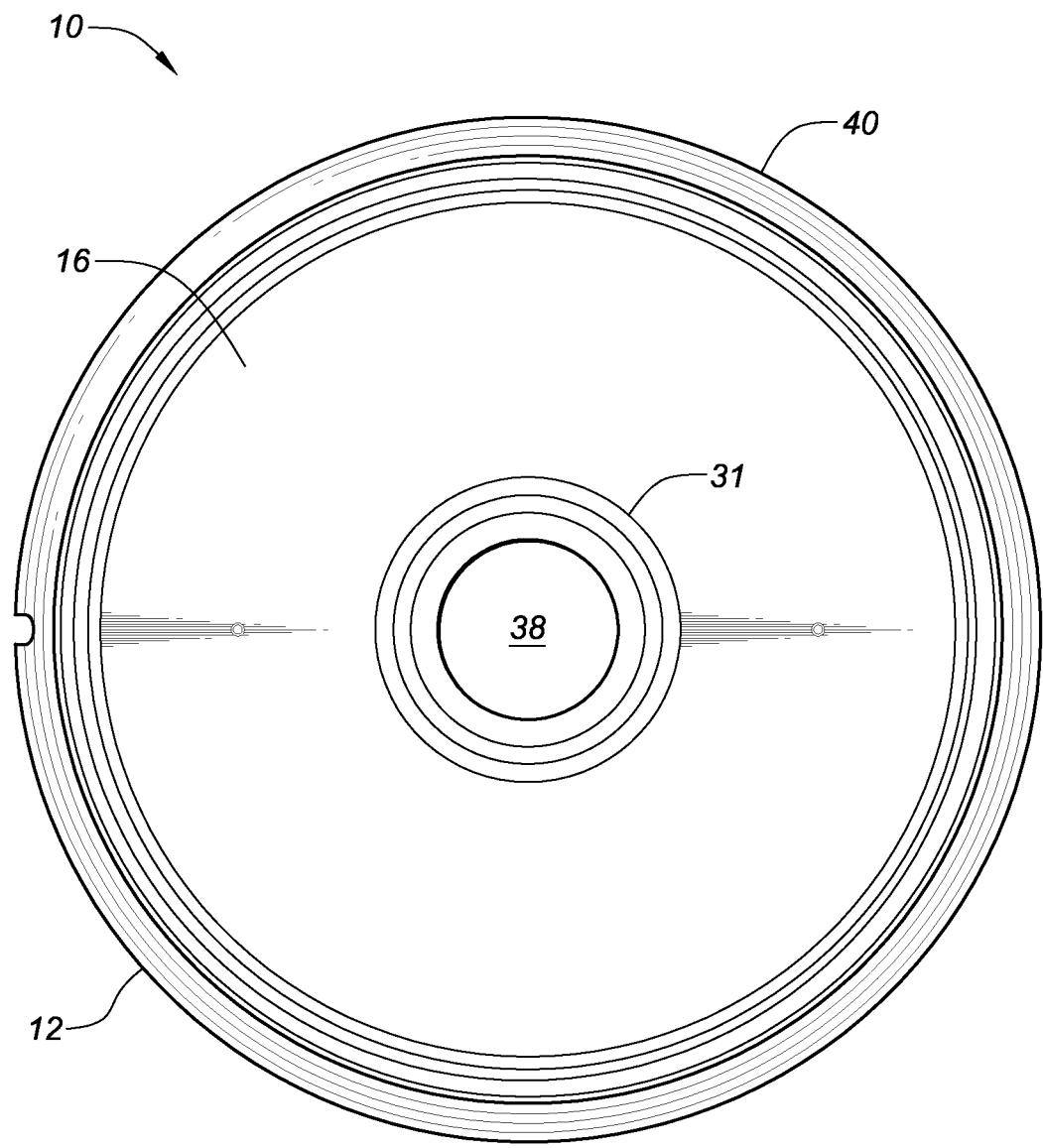
FIG. 11 is a top plan view of the diffuser stand of FIG. 1, according to an embodiment.

The plate 16 may also be of any shape or configuration. As shown in FIG. 11, the plate 16 may have a circular cross-section. In one embodiment, the plate 16 may have a third aperture 31 extending through the plate 16 along the longitudinal axis 20. The plate 16 may also include a peripheral portion 40, such as a rim, for receiving or securing the electric diffuser.

Figure 10:
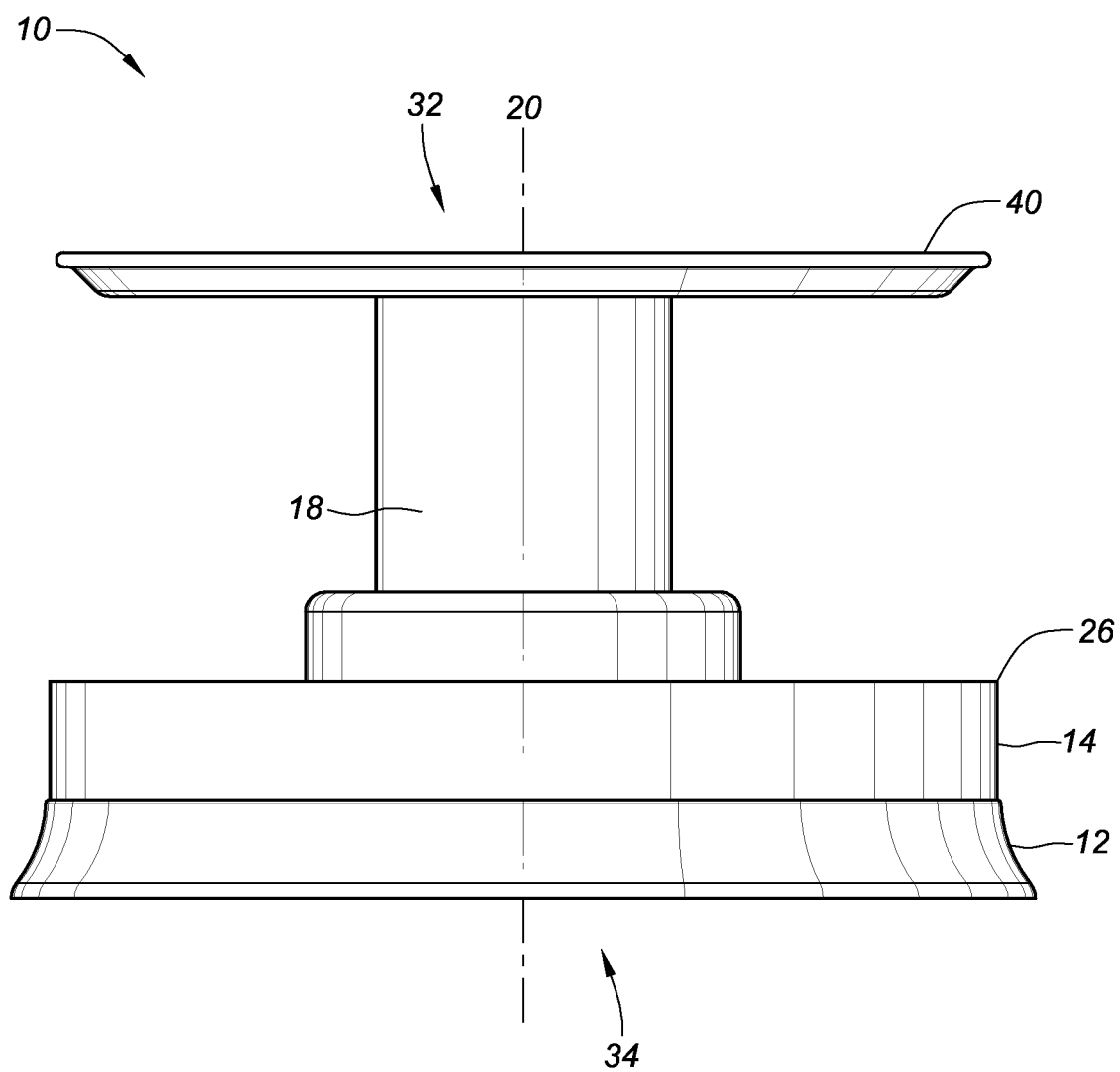
FIG. 10 is a back elevation view of the diffuser stand of FIG. 1, according to an embodiment.

As shown in FIG. 10, the shaft 18 may have a proximal end 32 and a distal end 34. The shaft 18 is hollow (shown in FIG. 1) along the longitudinal axis and has a first opening 36 at the distal end 34 (shown in FIG. 12) and a second opening 38 at the proximal end 32 (shown in FIG. 1). In one embodiment, the shaft 18 may be coupled to the base 12 at the distal end 34 with the first opening 36 of the shaft 18 aligned with the first aperture 22 of the base 18 along the longitudinal axis 20. Further, the shaft 18 may also be coupled to the plate 16 at the proximal end 32 with the second opening 38 of the shaft 18 aligned with the third aperture 31 of the plate 16 along the longitudinal axis 20. The shaft 18 may be of any shape or configuration. As shown in FIG. 1, the shaft 18 may have a cylindrical shape.

In one embodiment, the shaft may be configured and/or dimensioned to fit snugly within the third aperture 31 of the plate 16 and within the first aperture 22 of the base 12. Moreover, the second aperture 30 of the container 14 may be dimensioned for receiving the shaft 18 therethrough. In yet other embodiments, the shaft 18 may be formed as part of the base 12 or plate 16. In yet other embodiments, a portion of the shaft may be part of the base 12 and a portion may be part of the plate 16.

As can be appreciated, the electric diffuser may be positioned on the plate 16 of the diffuser stand 10. In one embodiment, the first aperture 22, the second aperture 30, the third aperture 30, the first opening 36, and the second opening 38 are concentric and form a passage dimensioned to allow the power cord of the electric diffuser to pass therethrough. Skilled artisans would appreciate that the diffuser stand 10 holds, supports and/or displays the electric diffuser while masking the power cord of the electric diffuser, allowing for the convenient selection of an essential oil from the container 14 without the power cord getting in the way. As such, in addition to providing psychological and physical well-being through smell, the electric diffuser apparatus of the present disclosure enhances the aesthetic quality of the visual component by masking the power cord of the electric diffuser to allow for the selection of an essential oil without the power cord getting in the way. The electric diffuser apparatus of the present disclosure also enhances the aesthetic quality of the visual component by visually displaying an array of essential oils for the user to enjoy and select from, which further enhances the quality of the touch component.

As may be seen in FIG. 5, the base 12 may have a notch to allow the power cord to exit the base 12.

In a preferred embodiment, the container 14 is rotatably coupled to the base 12 such that the container, and the plurality of compartments, can be rotated around by a user to allow observation and selection of the essential oils to use in the diffuser. In addition, plate 16 may also be rotatably coupled to the shaft 18 such that the plate 16 can also be rotated around and accordingly, the diffuser easily rotated around.

Although the various inventive aspects are herein disclosed in the context of certain preferred embodiments, implementations, and examples, it will be understood by those skilled in the art that the present invention extends beyond the specifically disclosed embodiments to other alternative embodiments and/or uses of the invention and obvious modifications and equivalents thereof. In addition, while a number of variations of the inventive aspects have been shown and described in detail, other modifications, which are within their scope will be readily apparent to those of skill in the art based upon this disclosure. It should be also understood that the scope this disclosure includes the various combinations or sub-combinations of the specific features and aspects of the embodiments disclosed herein, such that the various features, modes of implementation, and aspects of the disclosed subject matter may be combined with or substituted for one another. Thus, it is intended that the scope of the present invention herein disclosed should not be limited by the particular disclosed embodiments or implementations described above, but should be determined only by a fair reading of the claims.

Similarly, this disclosure is not be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

Further, all claim terms should be interpreted in their most expansive forms so as to afford the applicant the broadest coverage legally permissible. Although the embodiments have been described with reference to the drawings and specific examples, it will readily be appreciated by those skilled in the art that many modifications and adaptations of the processes, methods and apparatuses described herein are possible without departure from the spirit and scope of the embodiments as claimed herein. Thus, it is to be clearly understood that this description is made only by way of example and not as a limitation on the scope of the embodiments as claimed below.

What is claimed is:

1. A stand for an electric diffuser comprising:
a base having a first aperture, the first aperture extending through the base along a longitudinal axis of the stand;
a container rotatably coupled to the base, the container having a plurality of compartments dimensioned for receiving a plurality of essential oil bottles, the container having a second aperture, the second aperture extending through the container along the longitudinal axis;
a plate having a third aperture, the third aperture extending through the plate along the longitudinal axis; and
a shaft having a proximal end and a distal end, wherein the shaft is hollow along the longitudinal axis and has a first opening at the distal end and a second opening at the proximal end, the shaft is coupled to the base at the distal end and the first opening of the shaft is aligned with the first aperture of the base along the longitudinal axis, the shaft is coupled to the plate at the proximal end and the second opening of the shaft is aligned with the third aperture of the plate along the longitudinal axis,
wherein the first aperture, the second aperture, the third aperture, the first opening and the second opening form a passage that extends through the stand for an electric diffuser.

2. The stand of claim 1,
wherein the plate has a flat upper surface designed to support an electric diffuser
and allow a power cord to pass through the third aperture of the plate, the first opening and second opening of the hollow shaft, and the first aperture of the base.

3. The stand of claim 1, wherein the second aperture of the container is dimensioned for receiving the shaft therethrough.

4. The stand of claim 1, wherein the plate has a peripheral portion for receiving the electric diffuser.

5. The stand of claim 1, wherein the container and the shaft are cylindrical.

6. The stand of claim 1, wherein the shaft is configured and dimensioned to fit snugly within the third aperture of the plate.

7. The stand of claim 1, wherein the shaft is configured and dimensioned to fit snugly within the first aperture of the base.

8. The stand of claim 1, wherein the base, container and plate all have a circular cross-section.

9. The stand of claim 8, wherein each compartment in the plurality of compartments has a circular cross-section.

10. A diffuser stand for an electric diffuser comprising:
a circular base having a first aperture, the first aperture extending through the base along a longitudinal axis of the diffuser stand;
a cylindrical container rotatably coupled to the base, the cylindrical container having a plurality of compartments arranged generally equidistant to a peripheral cylindrical surface, the plurality of compartments are dimensioned for receiving a plurality of essential oil bottles wherein each compartment in the plurality of compartments is a cavity with an open top that extends down into the container from an upper surface of the container, the container having a second aperture, the second aperture extending through the container along the longitudinal axis;
a plate having a third aperture, the third aperture extending through the plate along the longitudinal axis; and
a shaft having a proximal end and a distal end, wherein the shaft is hollow along the longitudinal axis and has a first opening at the distal end and a second opening at the proximal end, the shaft is coupled to the base at the distal end and the first opening of the shaft is aligned with the first aperture of the base along the longitudinal axis, the shaft is coupled to the plate at the proximal end and the second opening of the shaft is aligned with the third aperture of the plate along the longitudinal axis,
wherein the first aperture, the second aperture, the third aperture, the first opening and the second opening are concentric and forming a passage that extends through the stand for an electric diffuser.

11. The diffuser stand of claim 10,
wherein the plate has a flat upper surface designed to support an electric diffuser, and
allow a power cord to pass through the third aperture of the plate, the first opening and second opening of the hollow shaft, and the first aperture of the base.

12. The diffuser stand of claim 10, wherein the second aperture of the container is dimensioned for receiving the shaft therethrough.

13. The diffuser stand of claim 10, wherein the plate has a peripheral portion for securing the electric diffuser.

14. The diffuser stand of claim 10, wherein the shaft is configured and dimensioned to fit snugly within the third aperture of the plate.

15. The diffuser stand of claim 10, wherein the shaft is configured and dimensioned to fit snugly within the first aperture of the base.

16. The diffuser stand of claim 10, wherein the each compartment in the plurality of compartments has a circular cross-section.

* * * * *